United States Patent
Cook et al.

(10) Patent No.: US 9,862,606 B1
(45) Date of Patent: Jan. 9, 2018

(54) CARBON ALLOTROPES

(71) Applicant: Lyten, Inc., Sunnyvale, CA (US)

(72) Inventors: Daniel Cook, Woodside, CA (US); Hossein-Ali Ghezelbash, Santa Clara, CA (US); Bryce H. Anzelmo, Mountain View, CA (US); David Tanner, San Jose, CA (US); Shreeyukta Singh, Sunnyvale, CA (US)

(73) Assignee: Lyten, Inc., Sunnyvale, CA (US)

( * ) Notice: Subject to any disclaimer, the term of this patent is extended or adjusted under 35 U.S.C. 154(b) by 0 days.

(21) Appl. No.: 15/594,032

(22) Filed: May 12, 2017

Related U.S. Application Data

(63) Continuation-in-part of application No. 15/470,450, filed on Mar. 27, 2017.

(51) Int. Cl.
*C01B 31/02* (2006.01)
*C01B 31/04* (2006.01)
(Continued)

(52) U.S. Cl.
CPC ........ *C01B 31/0213* (2013.01); *B22F 1/0025* (2013.01); *B82Y 30/00* (2013.01);
(Continued)

(58) Field of Classification Search
CPC ... C01B 31/0213; C01B 31/022; C01B 31/04; C01B 31/0423; C01B 31/0446; B22F 1/0025; B82Y 30/00; B82Y 40/00; C08J 5/005; C22C 1/058; G01N 21/65; C07C 2604/00
(Continued)

(56) References Cited

U.S. PATENT DOCUMENTS 3,217,056 A   11/1965   Kurt et al.
3,409,695 A   11/1968   Kurt et al.
(Continued)

FOREIGN PATENT DOCUMENTS

CN      1207189 C      6/2005
CN      100368080      2/2008
(Continued)

OTHER PUBLICATIONS

Definition of coating, accessed online at https://www.merriam-webster.com/dictionary/coating on Jul. 24, 2017.*
(Continued)

*Primary Examiner* — Daniel C McCracken
(74) *Attorney, Agent, or Firm* — The Mueller Law Office, P.C.

(57) ABSTRACT

A nanoparticle or agglomerate which contains connected multi-walled spherical fullerenes coated in layers of graphite. In different embodiments, the nanoparticles and agglomerates have different combinations of: a high mass fraction compared to other carbon allotropes present, a low concentration of defects, a low concentration of elemental impurities, a high Brunauer, Emmett and Teller (BET) specific surface area, and/or a high electrical conductivity. Methods are provided to produce the nanoparticles and agglomerates at a high production rate without using catalysts.

27 Claims, 9 Drawing Sheets

(51) Int. Cl.
*C08J 5/00* (2006.01)
*C22C 1/05* (2006.01)
*B82Y 40/00* (2011.01)
*B82Y 30/00* (2011.01)
*G01N 21/65* (2006.01)
*B22F 1/00* (2006.01)

(52) U.S. Cl.
CPC ............ *B82Y 40/00* (2013.01); *C01B 31/022* (2013.01); *C01B 31/04* (2013.01); *C01B 31/0423* (2013.01); *C01B 31/0446* (2013.01); *C08J 5/005* (2013.01); *C22C 1/058* (2013.01); *G01N 21/65* (2013.01); *C07C 2604/00* (2017.05)

(58) Field of Classification Search
USPC ............... 423/445 B; 977/734–741, 842–848
See application file for complete search history.

(56) References Cited

U.S. PATENT DOCUMENTS

| | | |
|---|---|---|
| 3,706,445 A | 12/1972 | Gentry |
| 5,321,191 A | 6/1994 | Alagy et al. |
| 5,572,866 A | 11/1996 | Loving |
| 5,693,173 A | 12/1997 | Colombo et al. |
| 5,985,232 A | 11/1999 | Howard et al. |
| 6,599,492 B2 | 7/2003 | Iwamura et al. |
| 6,692,718 B1 | 2/2004 | Osawa |
| 6,884,405 B2 | 4/2005 | Ryzhkov |
| 7,022,149 B2 | 4/2006 | Krause et al. |
| 7,790,243 B2 | 9/2010 | Radhakrishnan et al. |
| 7,981,396 B2 | 7/2011 | Harutyunyan |
| 8,034,321 B2 | 10/2011 | Mauthner et al. |
| 8,147,765 B2 | 4/2012 | Muradov et al. |
| 8,475,760 B2 | 7/2013 | Rajala et al. |
| 8,992,880 B2 | 3/2015 | Terayama et al. |
| 9,051,185 B2 | 6/2015 | Levendis et al. |
| 9,171,679 B2 | 10/2015 | Gogotsi et al. |
| 9,576,694 B2 | 2/2017 | Gogotsi et al. |
| 2003/0138365 A1 | 7/2003 | Obidniak et al. |
| 2004/0265211 A1 | 12/2004 | Dillon et al. |
| 2005/0003247 A1 | 1/2005 | Pham |
| 2005/0121309 A1 | 6/2005 | Chhowalla et al. |
| 2006/0078488 A1 | 4/2006 | Suemura et al. |
| 2007/0186470 A1 | 8/2007 | Ennis |
| 2009/0220767 A1 | 9/2009 | Schlogl et al. |
| 2010/0233366 A1 | 9/2010 | Fukushima et al. |
| 2011/0033639 A1 | 2/2011 | Coll et al. |
| 2011/0059006 A1 | 3/2011 | Donnet et al. |
| 2012/0107525 A1 | 5/2012 | Ohmae |
| 2012/0189530 A1 | 7/2012 | Marmaro et al. |
| 2012/0258374 A1 | 10/2012 | Raston et al. |
| 2014/0238842 A1 | 8/2014 | Gokhale et al. |
| 2015/0023858 A1 | 1/2015 | Tour et al. |
| 2016/0137506 A1 | 5/2016 | Arnault et al. |
| 2016/0141114 A1 | 5/2016 | Shelke et al. |
| 2016/0172123 A1 | 6/2016 | Yang et al. |

FOREIGN PATENT DOCUMENTS

| | | |
|---|---|---|
| CN | 101580241 A | 11/2009 |
| CN | 101885481 A | 11/2010 |
| CN | 201789030 U | 4/2011 |
| CN | 101905881 B | 5/2013 |
| CN | 103382025 B | 1/2015 |
| CN | 105833797 A | 8/2016 |
| CN | 106098944 A | 11/2016 |
| EP | 0808682 A3 | 3/2000 |
| EP | 1469941 B1 | 10/2007 |
| JP | H0290939 A | 3/1990 |
| JP | H05208805 A | 8/1993 |
| JP | 2003212502 | 7/2003 |
| JP | 3437066 B2 | 8/2003 |
| JP | 3544267 B2 | 7/2004 |
| JP | 4411039 B2 | 2/2010 |
| JP | 2012059462 A | 3/2012 |
| JP | 5162061 B2 | 3/2013 |
| JP | 2003206102 | 7/2013 |
| JP | 5298309 B2 | 9/2013 |
| JP | 5375197 B2 | 12/2013 |
| JP | 5649186 B2 | 1/2015 |
| JP | 3044934 B2 | 12/2016 |
| WO | 2007001412 A2 | 1/2007 |
| WO | 2016040948 A1 | 3/2016 |

OTHER PUBLICATIONS

Definition of coat, accessed online at https://www.merriam-webster.com/dictionary/coat on Jul. 24, 2017.*
Dresselhaus, et al., Science of Fullerenes and Carbon Nanotubes, pp. 60-79 (Academic Press 1996).*
Scientific Background on the Nobel Prize in Physics 2010 Graphene compiled by the Class for Physics of the Royal Swedish Academy of Sciences, pp. 1-10 (2010).*
Obraztsova, et al., Raman Identification of Onion-Like Carbon, Carbon 1998; 36(5-6): 821-826.*
Abanades et al., Experimental analysis of direct thermal methane cracking, International Journal of Hydrogen Energy, vol. 36, Issue 20, Oct. 2011, pp. 12877-12886.
Abbas and Wan Daud, Hydrogen production by methane decomposition: A review, International Journal of Hydrogen Energy, vol. 35, Issue 3, Feb. 2010, pp. 1160-1190.
Ahmed et al., Decomposition of hydrocarbons to hydrogen and carbon, Applied Catalysis A: General vol. 359, Issues 1-2, May 2009, pp. 1-24.
Alexandrou et al., Structure of carbon onions and nanotubes formed by arc in liquids, Journal of Chemical Physics, vol. 120, No. 2, Jan. 2004, pp. 1055-1058.
Asokan et al., Microwave irradiation on carbon black: Studies on the transformation of particles into nano-balls, nano-sticks and nano-onion like structures, Journal of Physics and Chemistry of Solids, vol. 99, Dec. 2016, pp. 173-181.
Beguin et al., Carbons and Electrolytes for Advanced Supercapacitors. Adv. Mater., 26, Feb. 2014, pp. 2219-2251.
Berezkin, Fullerenes as nuclei of carbon black particles, Physics of the Solid State, vol. 42, No. 3, Mar. 2000, p. 580-585.
Berezkin, Nucleation and Growth of Closed Many-Layer Carbon Particles, Phys. Stat. Sol. (b), 226, Jul. 2001, pp. 271-284.
Biomedical Engineering Desk Reference. Oxford: Academic Press, 2009, pp. iii-vi, 267, Print.
Bu, Synthesis of graphitic carbon nano-onions for dye sensitized solar cells, Solar Energy, vol. 105, Jul. 2014, pp. 236-242.
Buchholz et al., Mechanism for the growth of multiwalled carbon-nanotubes from carbon black, Carbon, vol. 41, Issue 8, Mar. 2003, pp. 1625-1634.
Bushueva et al., Double layer supercapacitor properties of onion-like carbon materials, Phys. Status Solidi B, vol. 245, No. 10, Oct. 2008, pp. 2296-2299.
Bystrzejewski et al., Catalyst-free synthesis of onion-like carbon nanoparticles, New Carbon Materials, vol. 25, Issue 1, Feb. 2010, pp. 1-8.
Cabioch et al., Fourier transform infra-red characterization of carbon onions produced by carbon-ion implantation, Chemical Physics Letters 285(3), Mar. 1998, pp. 216-220.
Cadez et al., Influence of hydrocarbons on vibrational excitation of $H_2$ molecules, Nuclear Engineering and Design 241, Apr. 2011), 1267-1271.
Chen et al., New method of carbon onion growth by radio-frequency plasma-enhanced chemical vapor deposition, Chemical Physics Letters 336, Mar. 2001, pp. 201-204.
Choucair and Stride, The gram-scale synthesis of carbon onions, Carbon, vol. 50, Issue 3, Mar. 2012, pp. 1109-1115.
Chuung et al., Flame synthesis of carbon nano-onions enhanced by acoustic modulation, Nanotechnology, vol. 21, No. 43, Oct. 2010, 11 pages.
Deshmukh et al., Carbon spheres, Materials Science and Engineering: R: Reports, vol. 70, Issue 1-2, Sep. 20, 2010, pp. 1-28.

(56) References Cited

OTHER PUBLICATIONS

Dhand et al., Flame synthesis of carbon nano onions using liquefied petroleum gas without catalyst, Materials Science and Engineering: C, vol. 33, Issue 2, Mar. 2013, pp. 758-762.
Dorobantu et al., Pulse Laser Ablation System for Carbon Nano-Onions Fabrication, Surface Engineering and Applied Electrochemistry, vol. 50, Issue 5, Sep. 2014, pp. 19-23.
Fan et al., The production of onion-like carbon nanoparticles by heating carbon in a liquid alcohol, Journal of Materials Chemistry, 22, Issue 19, May 2012, pp. 9794-9797.
Fu et al, Synthesis of Nano-structured Onion-like Fullerenes by MW Plasma, Journal of Inorganic Materials, vol. 21, No. 3, May 2006, 576-582.
Gao et al., Chemical activation of carbon nano-onions for high-rate supercapacitor electrodes, Carbon, vol. 51, Jan. 2013, pp. 52-58.
Gao et al., Growth of Carbon Nano-Onions in the Open Air by Laser Resonant Excitation of Precursor Molecules, Jan. 2010, 5 pages.
Gao et al., Resonant excitation of precursor molecules in improving the particle crystallinity, growth rate and optical limiting performance of carbon nano-onions, Nanotechnology, 22, Apr. 2011, 6 pages.
Grieco et al., Fullerenic carbon in combustion-generated soot, Carbon, vol. 38, Issue 4, Dec. 2000, pp. 597-614.
Gubarevich et al., Onion-like carbon deposition by plasma spraying of nanodiamonds, Carbon, vol. 41, Issue 13, Jul. 2003, pp. 2601-2606.
Guo and Jayatissa, Growth of Carbon Nanotubes on Metallic Catalyst by CVD, Proceedings of IMECE2006, 2006 ASME International Mechanical Engineering Congress and Exposition, Nov. 5-10, 2006, Chicago, Illinois, USA, 5 pages.
He et al., TEM investigation on the initial stage growth of carbon onions synthesized by CVD, Journal of Alloys and Compounds, vol. 452, Issue 2, Mar. 2008, pp. 258-262.
He et al., Effect of annealing on the structure of carbon onions and the annealed carbon coated Ni nanoparticles fabricated by chemical vapor deposition, Journal of Alloys and Compounds, vol. 472, Issue 1, Mar. 2009, pp. 230-233.
Hirata and Igarashi, Solid Lubricant Properties of Carbon Onions Prepared by Heat Treatment of Diamond Fine Particles, Journal of the Japan Society for Precision Engineering, vol. 69, No. 5, 2003 pp. 683-687, Released Apr. 10, 2009.
Hou et al., High-yield synthesis of carbon nano-onions in counterflow diffusion flames, Carbon, vol. 47, Issue 4, Apr. 2009, pp. 938-947.
Hydrogen Atom Beam Source HABS, MBE Komponenten, Dr. Eberl, www.mbe-components.com, Accessed on Feb. 10, 2017, 2 pages.
Iijima, Direct observation of the tetrahedral bonding in graphitized carbon black by high resolution electron microscopy, Journal of Crystal Growth, vol. 50, Issue 3, Nov. 1980, pp. 675-683.
Inaba and Hirata, Lubrication Property of Carbon Onions on Silicon Surface with Fine Patterns, Journal of the Japan Society for Precision Engineering, vol. 76, No. 1, Jul. 2010 p. 59-63.
Jackel et al., Comparison of carbon onions and carbon blacks as conductive additives for carbon supercapacitors in organic electrolytes, Journal of Power Sources, vol. 272, Dec. 25, 2014, pp. 1122-1133.
Jiang et al., Structure and electromagnetic properties of both regular and defective onion-like carbon nanoparticles, carbon, vol. 95, Dec. 2015, pp. 910-918.
Kaito and Hirata, Synthesis of Numerous Onion-like Fullerenes and Its Application to Solid Lubricant, Japan Society for Precision Engineering, vol. 67, No. 7, 2001, pp. 1175-1179, Released Apr. 2009.
Ko et al., Inherently-Forced Tensile Strain in Nanodiamond-Derived Onion-like Carbon: Consequences in Defect-Induced Electrochemical Activation, Scientific Reports, Apr. 2016, 10 pages.
Kobayashi, Formation of Carbon Onion from Heavily Shocked SiC, Chemistry of Materials, 15 (14), Jun. 2003, pp. 2681-2683.

Kogo and Hirata, Study on applicability of carbon onions as nano-abrasives, Japan Society for Precision Engineering, vol. 77, No. 3, Sep. 2011, pp. 311-315.
Konno et al, Direct Preparation of Hydrogen and Carbon Nanotubes by Microwave Plasma Decomposition of Methane over Fe/Si Activated by Biased Hydrogen Plasma, Green and Sustainable Chemistry, 2013, 3, 19-25, http://dx.doi.org/10.4236/gsc.2013.31004 Published Online Feb. 2013 (http://www.scirp.org/journal/gsc).
Krishnamurthy, Formation of onion-like carbon from the evaporation of ultra-dispersed nanodiamonds, Carbon, vol. 52, Feb. 2013, pp. 145-149.
Kromka et al., Investigation of Carburisation of Tungsten-Carbide Formation by Hot-Filament CVD Technique, Acta Physica Slovaca, 51(6), 359-368, Dec. 2001.
Kuznetsov et al., Onion-like carbon from ultra-disperse diamond, Chemical Physics Letters, vol. 222, Issue 4, May 1994, pp. 343-348.
Kwan, Hot-Filament Chemical Vapor Deposition of Selectively Deposited Diamond and Silicone Thin Films, Submitted to the Department of Chemical Engineering, Massachusetts Institute of Technology, Jul. 15, 1997, 183 pages.
Macutkevic et al., Dielectric Properties of Onion-Like Carbon and Detonation Nanodiamond/Polydimethysiloxane Composites, Polymer Composits, vol. 36, Issue 11, Nov. 2015, pp. 2084-2092.
Merijs-Meri et al., Carbon Nanotubes and Carbon Onions for Modification of Styrene—Acrylate Copolymer Nanocomposites, Polymer Composites, vol. 36, Issue 6, Jun. 2015, pp. 1048-1054.
MGC Series Thermal Gas Cracker, Mantis Deposition Ltd, Accessed on Feb. 10, 2017, 2 pages.
Moustakas, The Role of the Tungsten Filament in the Growth of Polycrystalline Diamond Films by Filament-assisted CVD of Hydrocarbons, Solid State Ionics, vols. 32-33, Part 2, Feb.-Mar. 1989, pp. 861-868.
Muradov et al., Autothermal catalytic pyrolysis of methane as a new route to hydrogen production with reduced $CO_2$ emissions, Catalysis Today 116, Jun. 2006, 281-288.
Namiki and Hirata, Low-temperature catalytic synthesis of carbon onions and evaluation of its solid lubricant property, Japan Society for Precision Engineering, vol. 2004S, 2004, pp. 723-724, Released May 2005.
Nos et al., Real-time monitoring of the silicidation process of tungsten filaments at high temperature used as catalysers for silane decomposition, Materials Chemistry and Physics vol. 143(2), Jan. 2014, pp. 881-888.
Office Action dated May 26, 2017 for U.S. Appl. No. 15/470,450.
Okoli et al., Influence of the Filament Material on Low-Pressure Hot-Filament CVD Diamond Deposition, Journal de Physique IV (Proceedings) 02(C2), Sep. 1991, 8 pages.
Onoue et al., Fine structure analysis of spherical carbon particles produced in a methane plasma, Diamond and Related Materials, vol. 27, Jul.-Aug. 2012, pp. 10-13.
Osawa et al., Revival of Carbon Nano-Onions : Towards Alternatives of the Arc Discharge Method for the Production of Fullerenes, Japan Society of Plasma Science and Nuclear Fusion Research, vol. 75, No. 8, 1999, pp. 914-920, Released Dec. 2000.
Ozawa and Osawa, Carbon Blacks as the Source Materials for Cabon Nanotechnology, 'Carbon Nanotechnology', Dai, L. (Ed.), Chapt. 6, p. 127-151, Elsevier: Dordrecht, Apr. 2006.
Pech et al., Ultrahigh-power micrometre-sized supercapacitors based on onion-like carbon, Nature Nanotechnology, vol. 5, Aug. 2010, pp. 651-654.
Plonska-Brzezinska and Echegoyen, Carbon nano-onions for supercapacitor electrodes: recent developments and applications, Journal of Materials Chemistry A, Issue 44, Nov. 2013, 11 pages.
Plonska-Brzezinska et al., The synthesis and characterization of carbon nano-onions produced by soultion ozonolysis, Carbon, vol. 49, Issue 15, Dec. 2011, pp. 5079-5089.
Portet et al., Electrochemical performance of carbon onions, nanodiamonds, carbon black and multiwalled nanotubes in electrical double layer capacitors, Carbon, vol. 45, Issue 13, Nov. 2007, pp. 2511-2518.
Qiao et al., Structural evolution and Raman study of nanocarbons from diamond nanoparticles, Chemical Physics Letters, vol. 429, Issue 4, Oct. 2006, pp. 479-482.

(56) References Cited

OTHER PUBLICATIONS

Studart et al., Arrested Coalescence of Particle-coated Droplets into Nonspherical Supracolloidal Structures, J. Phys. Chem. B, vol. 113 (12), Jan. 2009, pp. 3914-3919.
Szerencsi and Radnoczi, The mechanism of growth and decay of carbon nano-onions formed by ordering of amorphous particles, Vacuum, vol. 84, Issue 1, Aug. 2009, pp. 197-201.
Tapia et al., Carbon nano-allotropes produced by ultrasonication of few-layer graphene and fullerene, Carbon, vol. 99, Apr. 2016, pp. 541-546.
Thermal Gas Cracker TGC-H, SPECS GmbH, Components for Surface Analysis, www.specs.de, Access on Feb. 10, 2017, 2 pages.
Thune et al., Nucleation and growth of carbon onions synthesized by ion-implantation: a transmission electron microscopy study, Materials Letters, vol. 54, Issue 2, May 2002, pp. 222-228.
Tomita et al., Structure and electronic properties of carbon onions, Journal of Chemical Physics, vol. 114, No. 17 May 2001, pp. 7477-7482.
Ugarte, Curling and closure of graphitic networks under electron-beam irradiation, Letters to Nature, vol. 359,Oct. 1992, 707-709.
Ugarte, Graphitic Nanoparticles, MRS Bulletin, vol. 19, Issue 11 Nov. 1994, pp. 39-42.
Universal Thermal Cracker for Surface Science, Oxford Applied Research, www.oaresearch.co.uk, Accessed on Feb. 10, 2017, 2 pages.
Weingarth et al., Graphitization as a Universal Tool to Tailor the Potential-Dependent Capacitance of Carbon Supercapacitors. Adv. Energy Mater., 4, May 2014, 13 pages.
Yamada et al., Concentric shell carbon: curling process of graphitic layers, Carbon, vol. 35, Issue 12, Oct. 1997, pp. 1844-1846.
Yamada, Shock synthesis of concentric shell fullerene dimers and trimers, Carbon 42, Jun. 2004, pp. 3003-3042.
Yang et al., Synthesis of nano onion-like fullerenes by chemical vapor deposition using an iron catalyst supported on sodium chloride, J Nanopart Res, 13, May 2011, pp. 1979-1986.
Yeheskel and Epstein, Thermolysis of methane in a solar reactor for mass-production of hydrogen and carbon nano-materials, Carbon vol. 49, Issue 14, Nov. 2011, pp. 4695-4703.
Zeiger et al., Review: carbon onions for electrochemical energy storage, Journal of Materials Chemistry A, Issue 6, Mar. 2016, pp. 3172-3196.
Zeiger et al., Understanding structure and porosity of nanodiamond-derived carbon onions, Carbon, vol. 84, Apr. 2015, pp. 584-598.
Zeiger et al., Vacuum or flowing argon: What is the best synthesis atmosphere for nanodiamond-derived carbon onions for supercapacitor electrodes?, Carbon, vol. 94, Nov. 2015, pp. 507-517.
Zhang et al., Graphene-based materials as supercapacitor electrodes, Journal of Materials Chemistry, Issue 29, Aug. 2010, pp. 5983-5992.
Zhang et al., Methane Catalytic Cracking to Make Hydrogen and Graphitic Nano Carbons (Nanotubes, Microfibers, Microballs, Onions) with Zero Emission, Synthesis and Reactivity in Inorganic, Metal-Organic, and Nano-Metal Chemistry vol. 44 , Iss. 8, 2014, pp. 1116-1174, published online: Dec. 17, 2013.
Zheng et al., Development on the Preparation and Application of Onion-like Carbon, Journal of Inorganic Materials, vol. 30 No. 8, Aug. 2015, pp. 793-801.
Das et al., Formation of onion-like fullerene and chemically converted graphene-like nanosheets from low-quality coals: application in photocatalytic degradation of 2-nitrophenol, RSC Advances, Issue 42, Apr. 2016, 41 pages.
Xu, Prospects and research progress in nano onion-like fullerenes, New Carbon Materials, vol. 23, Issue 4, Mar. 2008, pp. 289-301.
Zhang et al., Microstructure and adsorption property of nanocarbide-derived carbon (CDC) synthesized at ambient temperature, Materials Letters, vol. 130, Sep. 2014, pp. 188-191.

* cited by examiner

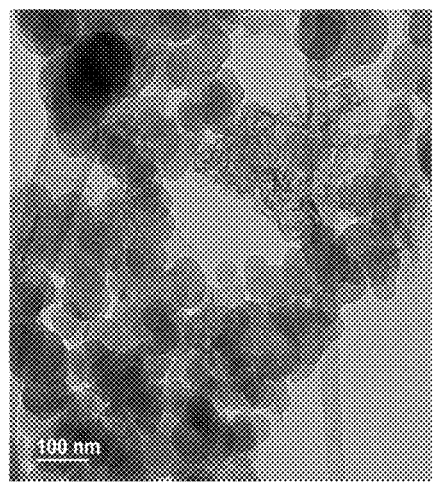
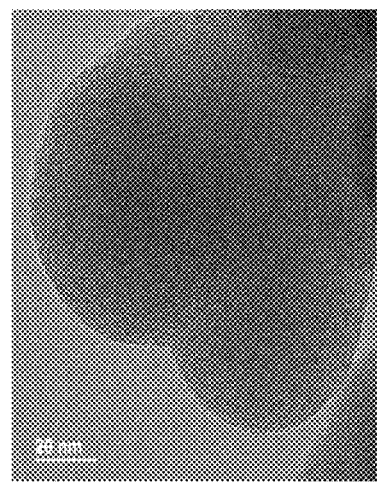
Fig. 4A       Fig. 4B
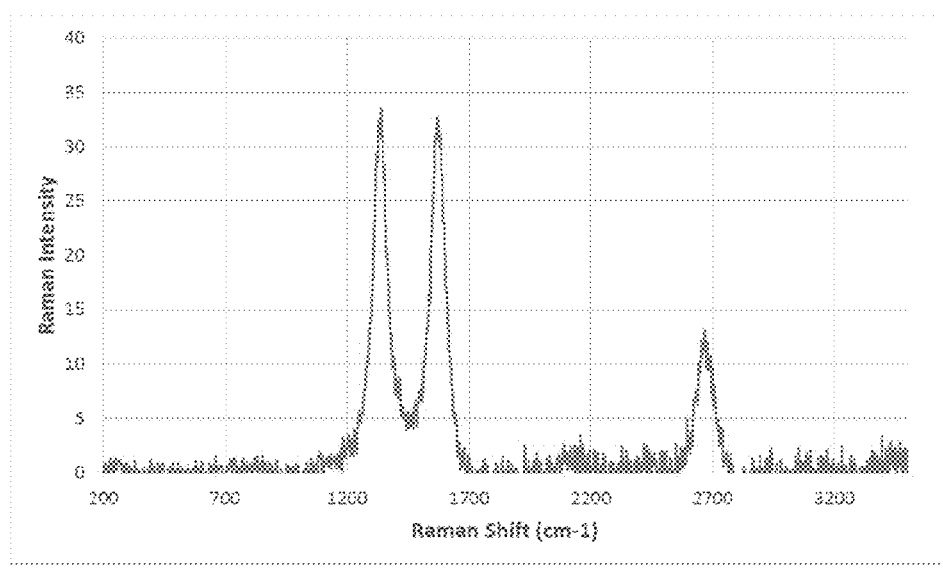
Fig. 4C

CARBON ALLOTROPES

CROSS-REFERENCE TO RELATED APPLICATIONS

This patent application is a continuation-in-part of U.S. patent application Ser. No. 15/470,450 filed Mar. 27, 2017, which is incorporated herein by reference.

BACKGROUND

Various crude or refined hydrocarbons (e.g., methane, ethane, propane, etc.) can be pyrolized or cracked to synthesize hydrogen and to produce higher-order carbon substances (e.g., graphene and fullerenes). However, some of the processes used to produce these higher-order carbon substances require the use of catalysts, such as metal catalysts. Additionally, some processes result in the presence of impurities within the higher-order carbon substances. Furthermore, some processes require the formation of a "seed" or "core" around which the higher-order carbon substances are formed.

Different allotropes of carbon can be generated by cracking hydrocarbons utilizing thermal processes. One example of a process for generating lower-order carbon substances (e.g., carbon black) is the solar thermolysis of methane (both with and without a catalyst) to produce hydrogen and carbon black. An example of a process for generating higher-order carbon substances is the catalytic decomposition of methane in a quartz tubular reactor to produce hydrogen and highly graphitic carbon nanotubes, microfibers, microballs, and carbon onions.

Some examples of higher-order carbon allotropes are shown in FIG. 1. FIG. 1A shows a schematic of graphite, where carbon forms multiple layers of a two-dimensional, atomic-scale, hexagonal lattice in which one atom forms each vertex. Graphene is a single layer of graphite. FIG. 1B shows a schematic of a carbon nanotube, where carbon atoms form a hexagonal lattice that is curved into a cylinder. Carbon nanotubes can also be referred to as cylindrical fullerenes. FIG. 1C shows a schematic of a C60 buckminsterfullerene, where a single layer of a hexagonal lattice of carbon atoms forms a sphere. Other spherical fullerenes exist that contain single layers of hexagonal lattices of carbon atoms, and can contain 60 atoms, 70 atoms, or more than 70 atoms. FIG. 1D shows a schematic of a carbon nano-onion from U.S. Pat. No. 6,599,492, which contains multiple concentric layers of spherical fullerenes.

SUMMARY

In some embodiments, a carbon nanoparticle comprises at least two connected multi-walled spherical fullerenes, and layers of graphene coating the connected multi-walled spherical fullerenes. In some embodiments, a Raman spectrum of the carbon nanoparticle using 532 nm incident light has a first Raman peak at approximately 1350 cm$^{-1}$ and a second Raman peak at approximately 1580 cm$^{-1}$, and a ratio of an intensity of the first Raman peak to an intensity of the second Raman peak is from 0.9 to 1.1. In some embodiments, a ratio of graphene to multi-walled spherical fullerenes is from 10% to 80%.

In some embodiments, the carbon nanoparticle described above contains multi-walled spherical fullerenes that do not comprise a seed particle or a void at the center of the multi-walled spherical fullerenes. In some embodiments, the carbon nanoparticle described above contains multi-walled spherical fullerenes that have an average diameter from 50 nm to 500 nm.

In some embodiments, a carbon aggregate comprises a plurality of the carbon nanoparticles described above, wherein a diameter across the carbon aggregate is from 10 microns to 500 microns. In some embodiments the carbon aggregate has a ratio of graphene to multi-walled spherical fullerenes from 10% to 80%. In some embodiments, the carbon aggregate has a ratio of carbon to other elements, except H, in the carbon aggregate is greater than 99.9%. In some embodiments, the carbon aggregate has a Brunauer, Emmett and Teller (BET) specific surface area of the carbon aggregate is from 10 m$^2$/g to 200 m$^2$/g. In some embodiments, a plurality of the carbon aggregates are compressed into a pellet, and the pellet has an electrical conductivity from 500 S/m to 20000 S/m.

In some embodiments, a mixture comprises a liquid and a plurality of the carbon nanoparticles described above. In some embodiments, a conductive ink comprises a plurality of the carbon nanoparticles described above.

In some embodiments a method comprises flowing a hydrocarbon feedstock process gas into a reaction zone, thermally cracking molecules of the feedstock process gas in the reaction zone, reacting the thermally cracked molecules to form carbon aggregates, each comprising at least two connected multi-walled spherical fullerenes coated in layers of graphene, and collecting the carbon aggregates. In some embodiments, a Raman spectrum of the carbon aggregates using 532 nm incident light has a first Raman peak at about 1350 cm-1 and a second Raman peak at about 1580 cm-1, and a ratio of an intensity of the first Raman peak to an intensity of the second Raman peak is from 0.9 to 1.1. In some embodiments, the collected carbon aggregates are size-reduced by mechanical means.

In some embodiments, the multi-walled spherical fullerenes produced using the method described above do not comprise a seed particle or a void at the center of the multi-walled spherical fullerenes. In some embodiments, the multi-walled spherical fullerenes produced using the method described above have an average diameter across the carbon aggregates is from 10 microns to 500 microns. In some embodiments, the multi-walled spherical fullerenes produced using the method described above have an average diameter from 50 nm to 500 nm. In some embodiments, the multi-walled spherical fullerenes produced using the method described above have a ratio of graphene to multi-walled spherical fullerenes is from 10% to 80%. In some embodiments, the multi-walled spherical fullerenes produced using the method described above have a ratio of carbon to other elements, except H, in the carbon aggregates is greater than 99.9%. In some embodiments, the multi-walled spherical fullerenes produced using the method described above have a Brunauer, Emmett and Teller (BET) specific surface area of the carbon aggregates is from 10 m2/g to 200 m2/g.

In some embodiments, the carbon aggregates are produced by the method described above, and then compressed into a pellet, wherein the pellet has an electrical conductivity from 500 S/m to 20000 S/m. In some embodiments, the carbon aggregates are produced by the method described above, using a gas resonance time of 0.1 seconds to 30 seconds. In some embodiments, the carbon aggregates are produced by the method described above, using a gas flow rate of 1 slm to 10 slm and a production rate from 10 g/hr to 200 g/hr.

In some embodiments, the carbon aggregates are produced by the method described above, and then postprocessed using a method selected from group consisting of chemical etching, thermal annealing, particle sintering, spark plasma sintering, steaming, filtering, lypolizing, processing using Hummers' method, doping, and adding elements.

BRIEF DESCRIPTION OF THE DRAWINGS

FIGS. 4A-4C show TEM images and Raman spectra from size-reduced carbon aggregates in a first example, in accordance with some embodiments.

DETAILED DESCRIPTION

Figure 1A:
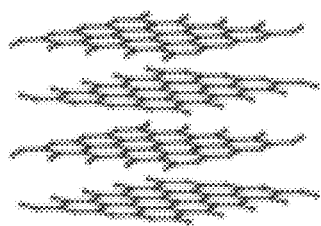
FIG. 1 is a schematic of carbon allotropes from the prior art.
Figure 1B:
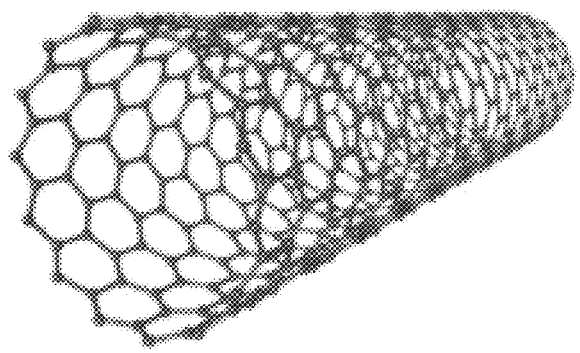
Figure 1C:
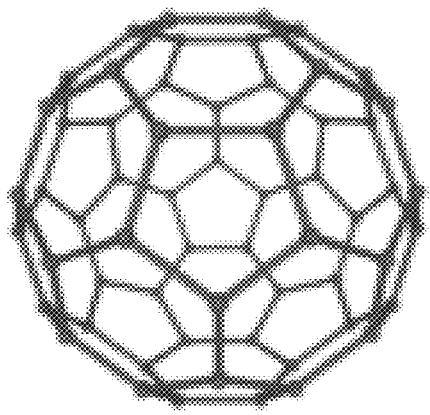
Figure 1D:
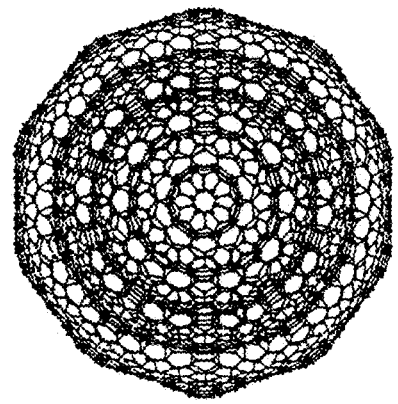
Figure 2:
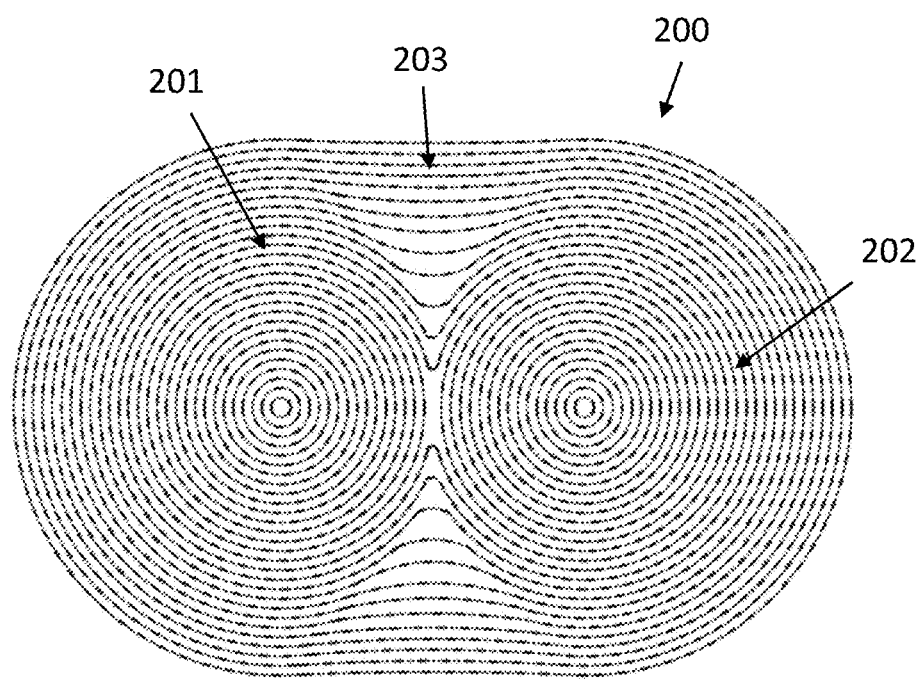
FIG. 2 is a schematic of idealized connected multi-walled spherical fullerenes, in accordance with some embodiments.

The present disclosure relates to carbon nanoparticles and aggregates that include different allotropes of (i.e., various forms of) carbon, including graphene, various fullerenes, and combinations thereof, as described below. In some embodiments, the carbon nanoparticles and aggregates are characterized by a high "uniformity" (i.e., high mass fraction of desired carbon allotropes), high degree of "order" (i.e., low concentration of defects), and/or high "purity" (i.e., low concentration of elemental impurities), in contrast to the lower uniformity, less ordered and lower purity particles achievable with conventional systems and methods. In some embodiments, the carbon nanoparticles and aggregates described herein are characterized by a size that is substantially larger than comparable prior art particles. In some embodiments, the carbon nanoparticles and aggregates described herein are characterized by a well-ordered structure with high purity as illustrated by an idealized carbon nanoparticle 200 shown in FIG. 2. The carbon allotrope in FIG. 2 contains two connected multi-walled spherical fullerenes (MWSFs) 201 and 202 with layers of graphene 203 coating the connected MWSFs 201 and 202). The allotrope shown in FIG. 2 is also core-less (i.e., does not contain a core of a material other than carbon at the center of the spherical fullerene). The idealized nanoparticle shown in FIG. 2 has high uniformity since the ratio of MWSFs to graphene is high, is well-ordered since there are no point defects (e.g., missing carbon atoms) and no distorted carbon lattices, and has a high purity since there are no elements (e.g., a core of impurities) other than carbon, in contrast with low uniformity mixtures of MWSFs mixed with other carbon allotropes, poorly-ordered MWSFs with many point defects and distorted lattices, and low purity MWSFs (e.g., with seed particles at the core). In other embodiments, the connected MWSFs do contain a core. In some embodiments, the core is a void, a carbon-based material that is not an MWSF (e.g., amorphous carbon), or a seed that is not carbon-based.

In some embodiments, the nanoparticles produced using the methods described herein contain MWSFs or connected MWSFs and have a high uniformity (e.g., a ratio of graphene to MWSF from 20% to 80%), a high degree of order (e.g., a Raman signature with an $I_D/I_G$ ratio from 0.95 to 1.05), and a high purity (e.g., the ratio of carbon to other elements, other than H, is greater than 99.9%). In some embodiments, the nanoparticles produced using the methods described herein contain MWSFs or connected MWSFs, and the MWSFs do not contain a core composed of impurity elements other than carbon. In some cases, the particles produced using the methods described herein are aggregates containing the nanoparticles described above with large diameters (e.g., greater than 10 microns across).

Conventional methods have been used to produce particles containing multi-walled spherical fullerenes (MWSFs) with a high degree of order, but the conventional methods lead to carbon products with a variety of shortcomings. For example, high temperature synthesis techniques lead to particles with a mixture of many carbon allotropes and therefore low uniformity (e.g., less than 20% fullerenes to other carbon allotropes) and/or small particle sizes (e.g., less than 1 micron, or less than 100 nm in some cases). Methods utilizing catalysts lead to products including the catalyst elements and therefore have low purity (e.g., less than 95% carbon to other elements). These undesirable properties also often lead to undesirable electrical properties of the resulting carbon particles (e.g., electrical conductivity less than 1000 S/m).

In some embodiments, the carbon nanoparticles and aggregates described herein are characterized by Raman spectroscopy that is indicative of the high degree of order, and the uniformity of the structure. In some embodiments, the uniform, ordered and/or pure carbon nanoparticles and aggregates described herein are produced using relatively high speed, low cost improved thermal reactors and methods, as described below. Additional advantages and/or improvements will also become apparent from the following disclosure.

In the present disclosure, the term "graphene" refers to an allotrope of carbon in the form of a two-dimensional, atomic-scale, hexagonal lattice in which one atom forms each vertex. The carbon atoms in graphene are sp2-bonded. Additionally, graphene has a Raman spectrum with two main peaks: a G-mode at approximately 1580 cm$^{-1}$ and a D-mode at approximately 1350 cm$^{-1}$ (when using a 532 nm excitation laser).

In the present disclosure, the term "fullerene" refers to a molecule of carbon in the form of a hollow sphere, ellipsoid, tube, or other shapes. Spherical fullerenes can also be referred to as Buckminsterfullerenes, or buckyballs. Cylindrical fullerenes can also be referred to as carbon nanotubes. Fullerenes are similar in structure to graphite, which is composed of stacked graphene sheets of linked hexagonal rings. Fullerenes may also contain pentagonal (or sometimes heptagonal) rings.

In the present disclosure, the term "multi-walled fullerene" refers to fullerenes with multiple concentric layers. For example, multi-walled nanotubes (MWNTs) contain multiple rolled layers (concentric tubes) of graphene. Multi-walled spherical fullerenes (MWSFs) contain multiple concentric spheres of fullerenes.

In the present disclosure, the term "nanoparticle" refers to a particle that has a size from 1 nm to 900 nm. The nanoparticle can include one or more type of structure (e.g., crystal structure, defect concentration, etc.), and one or more type of atom. The nanoparticle can be any shape, including but not limited to spherical shapes, spheroidal shapes, dumbbell shapes, cylindrical shapes, elongated cylindrical type shapes, rectangular prism shapes, disk shapes, wire shapes, irregular shapes, dense shapes (i.e., with few voids), porous shapes (i.e., with many voids), etc.

In the present disclosure, the term "aggregate" refers to a plurality of nanoparticles that are connected together by Van der Waals forces, by covalent bonds, by ionic bonds, by metallic bonds, or by other physical or chemical interactions. Aggregates can vary in size considerably, but in general are larger than about 500 nm.

In some embodiments, a carbon nanoparticle, as described herein, includes two or more connected multi-walled spherical fullerenes (MWSFs) and layers of graphene coating the connected MWSFs. In some embodiments, a carbon nanoparticle, as described herein, includes two or more connected multi-walled spherical fullerenes (MWSFs) and layers of graphene coating the connected MWSFs, and the MWSFs do not contain a core composed of impurity elements other than carbon. In some embodiments, a carbon nanoparticle, as described herein, includes two or more connected multi-walled spherical fullerenes (MWSFs) and layers of graphene coating the connected MWSFs, and the MWSFs do not contain a void (i.e., a space with no carbon atoms greater than approximately 0.5 nm, or 1 nm) at the center. In some embodiments, the connected MWSFs are formed of concentric, well-ordered spheres of sp2-hybridized carbon atoms, as contrasted with spheres of poorly-ordered, non-uniform, amorphous carbon particles.

In some embodiments, the nanoparticles containing the connected MWSFs have an average diameter in a range from 5 to 500 nm, or from 5 to 250 nm, or from 5 to 100 nm, or from 5 to 50 nm, or from 10 to 500 nm, or from 10 to 250 nm, or from 10 to 100 nm, or from 10 to 50 nm, or from 40 to 500 nm, or from 40 to 250 nm, or from 40 to 100 nm, or from 50 to 500 nm, or from 50 to 250 nm, or from 50 to 100 nm.

In some embodiments, the carbon nanoparticles described herein form aggregates, wherein many nanoparticles aggregate together to form a larger unit. In some embodiments, a carbon aggregate includes a plurality of carbon nanoparticles. A diameter across the carbon aggregate is in a range from 10 to 500 microns, or from 50 to 500 microns, or from 100 to 500 microns, or from 250 to 500 microns, or from 10 to 250 microns, or from 10 to 100 microns, or from 10 to 50 microns. In some embodiments, the aggregate is formed from a plurality of carbon nanoparticles, as defined above. In some embodiments, aggregates contain connected MWSFs. In some embodiments, the aggregates contain connected MWSFs with high uniformity (e.g., a ratio of graphene to MWSF from 20% to 80%), a high degree of order (e.g., a Raman signature with an $I_D/I_G$ ratio from 0.95 to 1.05), and a high purity (e.g., greater than 99.9% carbon).

One benefit of producing aggregates of carbon nanoparticles, particularly with diameters in the ranges described above, is that aggregates of particles greater than 10 microns are easier to collect than particles or aggregates of particles that are smaller than 500 nm. The ease of collection reduces the cost of manufacturing equipment used in the production of the carbon nanoparticles and increases the yield of the carbon nanoparticles. Additionally, particles greater than 10 microns in size pose fewer safety concerns compared to the risks of handling smaller nanoparticles, e.g., potential health and safety risks due to inhalation of the smaller nanoparticles. The lower health and safety risks, thus, further reduce the manufacturing cost.

In some embodiments, a carbon nanoparticle has a ratio of graphene to MWSFs from 10% to 90%, or from 10% to 80% or from 10% to 60%, or from 10% to 40%, or from 10% to 20%, or from 20% to 40%, or from 20% to 90%, or from 40% to 90%, or from 60% to 90%, or from 80% to 90%. In some embodiments, a carbon aggregate has a ratio of graphene to MWSFs is from 10% to 90%, or from 10% to 80% or from 10% to 60%, or from 10% to 40%, or from 10% to 20%, or from 20% to 40%, or from 20% to 90%, or from 40% to 90%, or from 60% to 90%, or from 80% to 90%. In some embodiments, a carbon nanoparticle has a ratio of graphene to connected MWSFs from 10% to 90%, or from 10% to 80% or from 10% to 60%, or from 10% to 40%, or from 10% to 20%, or from 20% to 40%, or from 20% to 90%, or from 40% to 90%, or from 60% to 90%, or from 80% to 90%. In some embodiments, a carbon aggregate has a ratio of graphene to connected MWSFs is from 10% to 90%, or from 10% to 80% or from 10% to 60%, or from 10% to 40%, or from 10% to 20%, or from 20% to 40%, or from 20% to 90%, or from 40% to 90%, or from 60% to 90%, or from 80% to 90%.

In some embodiments, Raman spectroscopy is used to characterize carbon allotropes to distinguish their molecular structures. For example, graphene can be characterized using Raman spectroscopy to determine information such as order/disorder, edge and grain boundaries, thickness, number of layers, doping, strain, and thermal conductivity. MWSFs have also been characterized using Raman spectroscopy to determine the degree of order of the MWSFs.

In some embodiments, Raman spectroscopy is used to characterize the structure of MWSFs or connected MWSFs. The main peaks in the Raman spectra are the G-mode and the D-mode. The G-mode is attributed to the vibration of carbon atoms in sp2-hybridized carbon networks, and the D-mode is related to the breathing of hexagonal carbon rings with defects. When using 532 nm incident light, the Raman G-mode is typically at 1582 cm$^{-1}$ for planar graphite, but can be downshifted for MWSFs or connected MWSFs (e.g., to 1565-1580 cm$^{-1}$). The D-mode is observed at approximately 1350 cm$^{-1}$ in the Raman spectra of MWSFs or connected MWSFs. The ratio of the intensities of the D-mode peak to G-mode peak (i.e., the $I_D/I_G$) is related to the degree of order of the MWSFs, where a lower $I_D/I_G$ indicates higher degree of order. An $I_D/I_G$ near or below 1 indicates a relatively high degree of order, and a $I_D/I_G$ greater than 1.1 indicates lower degree of order.

In some embodiments, a carbon nanoparticle or a carbon aggregate containing MWSFs or connected MWSFs, as described herein, has a Raman spectrum with a first Raman peak at about 1350 cm$^{-1}$ and a second Raman peak at about 1580 cm$^{-1}$, when using 532 nm incident light. In some embodiments, the ratio of an intensity of the first Raman peak to an intensity of the second Raman peak (i.e., the $I_D/I_G$) for the nanoparticles or the aggregates described herein is in a range from 0.95 to 1.05, or from 0.9 to 1.1, or from 0.8 to 1.2, or from 0.9 to 1.2, or from 0.8 to 1.1, or from 0.5 to 1.5, or less than 1.5, or less than 1.2, or less than 1.1, or less than 1, or less than 0.95, or less than 0.9, or less than 0.8.

In some embodiments, a carbon aggregate containing MWSFs or connected MWSFs, as defined above, has high purity. In some embodiments, the carbon aggregate containing MWSFs or connected MWSFs has a ratio of carbon to metals of greater than 99.99%, or greater than 99.95%, or greater than 99.9%, or greater than 99.8%, or greater than 99.5%, or greater than 99%. In some embodiments, the carbon aggregate has a ratio of carbon to other elements of greater than 99.99%, or greater than 99.95%, or greater than 99.9%, or greater than 99.5%, or greater than 99%, or greater than 90%, or greater than 80%, or greater than 70%, or greater than 60%. In some embodiments, the carbon aggregate has a ratio of carbon to other elements, except H, of greater than 99.99%, or greater than 99.95%, or greater than 99.9%, or greater than 99.8%, or greater than 99.5%, or greater than 99%, or greater than 90%, or greater than 80%, or greater than 70%, or greater than 60%.

In some embodiments, a carbon aggregate containing MWSFs or connected MWSFs, as defined above, has high specific surface area. In some embodiments, the carbon aggregate has a Brunauer, Emmett and Teller (BET) specific surface area from 10 to 200 $m^2/g$, or from 10 to 100 $m^2/g$, or from 10 to 50 $m^2/g$, or from 50 to 200 $m^2/g$, or from 50 to 100 $m^2/g$, or from 10 to 1000 $m^2/g$.

In some embodiments, a carbon aggregate containing MWSFs or connected MWSFs, as defined above, has high electrical conductivity. In some embodiments, a carbon aggregate containing MWSFs or connected MWSFs, as defined above, is compressed into a pellet and the pellet has electrical conductivity greater than 500 S/m, or greater than 1000 S/m, or greater than 2000 S/m, or greater than 3000 S/m, or greater than 4000 S/m, or greater than 5000 S/m, or greater than 10000 S/m, or greater than 20000 S/m, or greater than 30000 S/m, or greater than 40000 S/m, or greater than 50000 S/m, or greater than 60000 S/m, or greater than 70000 S/m, or from 500 S/m to 100000 S/m, or from 500 S/m to 1000 S/m, or from 500 S/m to 10000 S/m, or from 500 S/m to 20000 S/m, or from 500 S/m to 100000 S/m, or from 1000 S/m to 10000 S/m, or from 1000 S/m to 20000 S/m, or from 10000 to 100000 S/m, or from 10000 S/m to 80000 S/m, or from 500 S/m to 10000 S/m. In some cases, the density of the pellet is approximately 1 $g/cm^3$, or approximately 1.2 $g/cm^3$, or approximately 1.5 $g/cm^3$, or approximately 2 $g/cm^3$, or approximately 2.2 $g/cm^3$, or approximately 2.5 $g/cm^3$, or approximately 3 $g/cm^3$. Additionally, tests have been performed in which compressed pellets of the carbon aggregate materials have been formed with compressions of 2000 psi and 12000 psi and with annealing temperatures of 800 C and 1000 C. The higher compression and/or the higher annealing temperatures generally resulted in pellets with higher electrical conductivity, including in a range of 12410.0 S/m to 13173.3 S/m.

High Purity Carbon Allotropes Produced Using Thermal Processing Systems

In some embodiments, the carbon nanoparticles and aggregates described herein are produced using thermal reactors and methods, such as any appropriate thermal reactor and/or method described in the aforementioned U.S. patent application Ser. No. 15/470,450, which is assigned to the same assignee as the present application, and which is incorporated herein by reference as if fully set forth herein for all purposes. Additionally, precursors (e.g., including methane, ethane, propane, butane, and natural gas) can be used with the thermal reactors to produce the carbon nanoparticles and the carbon aggregates described herein.

In some embodiments, the carbon nanoparticles and aggregates described herein are produced using the thermal reactors with gas flow rates from 1 slm to 10 slm, or from 0.1 slm to 20 slm, or from 1 slm to 5 slm, or from 5 slm to 10 slm, or greater than 1 slm, or greater than 5 slm. In some embodiments, the carbon nanoparticles and aggregates described herein are produced using the thermal reactors with gas resonance times from 0.1 seconds to 30 seconds, or from 0.1 seconds to 10 seconds, or from 1 seconds to 10 seconds, or from 1 seconds to 5 seconds, from 5 seconds to 10 seconds, or greater than 0.1 seconds, or greater than 1 seconds, or greater than 5 seconds, or less than 30 seconds.

In some embodiments, the carbon nanoparticles and aggregates described herein are produced using the thermal reactors with production rates from 10 g/hr to 200 g/hr, or from 30 g/hr to 200 g/hr, or from 30 g/hr to 100 g/hr, or from 30 g/hr to 60 g/hr, or from 10 g/hr to 100 g/hr, or greater than 10 g/hr, or greater than 30 g/hr, or greater than 100 g/hr.

In some embodiments, thermal reactors (or cracking apparatuses) and methods can be used for refining, pyrolizing, dissociating or cracking feedstock process gases into constituent components to produce the carbon nanoparticles and the carbon aggregates described herein, as well as other solid and/or gaseous products (e.g., hydrogen gas and/or lower order hydrocarbon gases). The feedstock process gases generally include, for example, hydrogen gas (H2), carbon dioxide (CO2), C1-10 hydrocarbons, aromatic hydrocarbons, other hydrocarbon gases, natural gas, methane, ethane, propane, butane, isobutane, saturated/unsaturated hydrocarbon gases, ethene, propene, etc. and mixtures thereof. The carbon nanoparticles and the carbon aggregates can include, for example, multi-walled spherical fullerenes (MWSFs), connected MWSFs, carbon nanospheres, graphene, graphite, highly ordered pyrolytic graphite, single walled nanotubes, multi-walled nanotubes, other solid carbon products, and/or the carbon nanoparticles and the carbon aggregates described herein.

Some embodiments for producing the carbon nanoparticles and the carbon aggregates described herein include thermal cracking methods that use, for example, an elongated longitudinal heating element optionally enclosed within an elongated casing, housing or body of a thermal cracking apparatus. The body generally includes, for example, one or more tubes or other appropriate enclosures made of stainless steel, titanium, graphite, quartz, or the like. In some embodiments, the body of the thermal cracking apparatus is generally cylindrical in shape with a central elongate longitudinal axis arranged vertically and a feedstock process gas inlet at or near a top of the body. The feedstock process gas flows longitudinally down through the body or a portion thereof. In the vertical configuration, both gas flow and gravity assist in the removal of the solid products from the body of the thermal cracking apparatus.

The heating element generally includes, for example, a heating lamp, one or more resistive wires or filaments (or twisted wires), metal filaments, metallic strips or rods, and/or other appropriate thermal radical generators or elements that can be heated to a specified temperature (i.e., a molecular cracking temperature) sufficient to thermally crack molecules of the feedstock process gas. The heating element is generally disposed, located or arranged to extend centrally within the body of the thermal cracking apparatus along the central longitudinal axis thereof. For example, if there is only one heating element, then it is placed at or concentric with the central longitudinal axis, and if there is a plurality of the heating elements, then they are spaced or offset generally symmetrically or concentrically at locations near and around and parallel to the central longitudinal axis.

Thermal cracking to produce the carbon nanoparticles and aggregates described herein is generally achieved by passing the feedstock process gas over, in contact with, or within the vicinity of, the heating element within a longitudinal elongated reaction zone generated by heat from the heating element and defined by and contained inside the body to heat the feedstock process gas to or at a specified molecular cracking temperature. The reaction zone is considered to be the region surrounding the heating element and close enough to the heating element for the feedstock process gas to receive sufficient heat to thermally crack the molecules thereof. The reaction zone is thus generally axially aligned or concentric with the central longitudinal axis of the body.

In some embodiments, the thermal cracking is performed under a specified pressure. In some embodiments, the feedstock process gas is circulated around or across the outside surface of a container of the reaction zone or a heating chamber in order to cool the container or chamber and preheat the feedstock process gas before flowing the feedstock process gas into the reaction zone.

In some embodiments, the carbon nanoparticles and aggregates described herein and/or hydrogen gas are produced without the use of catalysts. In other words, the process is catalyst-free.

Some embodiments to produce the carbon nanoparticles and aggregates described herein using thermal cracking apparatuses and methods provide a standalone system that can advantageously be rapidly scaled up or scaled down for different production levels as desired. For example, some embodiments are scalable to provide a standalone hydrogen and/or carbon nanoparticle producing station system, a hydrocarbon source or a fuel cell station. Some embodiments can be scaled up to provide higher capacity systems, e.g., for a refinery or the like.

In some embodiments, a thermal cracking apparatus for cracking a feedstock process gas to produce the carbon nanoparticles and aggregates described herein includes a body, a feedstock process gas inlet, and an elongated heating element. The body has an inner volume with a longitudinal axis. The inner volume has a reaction zone concentric with the longitudinal axis. A feedstock process gas is flowed into the inner volume through the feedstock process gas inlet during thermal cracking operations. The elongated heating element is disposed within the inner volume along the longitudinal axis and is surrounded by the reaction zone. During the thermal cracking operations, the elongated heating element is heated by electrical power to a molecular cracking temperature to generate the reaction zone, the feedstock process gas is heated by heat from the elongated heating element, and the heat thermally cracks molecules of the feedstock process gas that are within the reaction zone into constituent components of the molecules.

In some embodiments, a method for cracking a feedstock process gas to produce the carbon nanoparticles and aggregates described herein includes providing a thermal cracking apparatus having an inner volume that has a longitudinal axis and an elongated heating element disposed within the inner volume along the longitudinal axis; heating the elongated heating element by electrical power to a molecular cracking temperature to generate a longitudinal elongated reaction zone within the inner volume; flowing a feedstock process gas into the inner volume and through the longitudinal elongated reaction zone, wherein the feedstock process gas is heated by heat from the elongated heating element; thermally cracking molecules of the feedstock process gas within the longitudinal elongated reaction zone into constituent components thereof (e.g., hydrogen gas and one or more solid products) as the feedstock process gas flows through the longitudinal elongated reaction zone; and collecting the constituent components.

In some embodiments, the feedstock process gas to produce the carbon nanoparticles and aggregates described herein includes a hydrocarbon gas, and the constituent components include hydrogen and the carbon nanoparticles and aggregates described herein. In some embodiments, the carbon nanoparticles and aggregates include two or more MWSFs and layers of graphene coating the MWSFs, and/or connected MWSFs and layers of graphene coating the connected MWSFs. In some embodiments, the feedstock process gas is preheated (e.g., to 100-500° C.) by flowing the feedstock process gas through a gas preheating region between a heating chamber and a shell of the thermal cracking apparatus before flowing the feedstock process gas into the inner volume. In some embodiments, a gas having nanoparticles therein is flowed into the inner volume and through the longitudinal elongated reaction zone to mix with the feedstock process gas; and a coating of a solid product (e.g., layers of graphene) is formed around the nanoparticles.

Additional information and embodiments for thermal cracking system methods and apparatuses to produce the carbon nanoparticles and aggregates described herein are described in the aforementioned U.S. patent application Ser. No. 15/470,450.

Post-Processing High Purity Carbon Allotropes

In some embodiments, the carbon nanoparticles and aggregates containing multi-walled spherical fullerenes (MWSFs) or connected MWSFs described herein are produced and collected, and no post-processing is done. In other embodiments, the carbon nanoparticles and aggregates containing multi-walled spherical fullerenes (MWSFs) or connected MWSFs described herein are produced and collected, and some post-processing is done. Some examples of post-processing include mechanical processing, such as ball milling, grinding, attrition milling, micro-fluidizing, and other techniques to reduce the particle size without damaging the MWSFs. Some examples of post-processing include exfoliation processes such as sheer mixing, chemical etching, oxidizing (e.g., Hummer method), thermal annealing, doping by adding elements during annealing (e.g., S, and N), steaming, filtering, and lypolizing, among others. Some examples of post-processing include sintering processes such as SPS (Spark Plasma Sintering, i.e., Direct Current Sintering), Microwave, and UV (Ultra-Violet), which can be conducted at high pressure and temperature in an inert gas. In some embodiments, multiple post-processing methods can be used together or in series. In some embodiments, the post-processing will produce functionalized carbon nanoparticles or aggregates containing multi-walled spherical fullerenes (MWSFs) or connected MWSFs.

In some embodiments, the materials are mixed together in different combinations. In some embodiments, different carbon nanoparticles and aggregates containing MWSFs or connected MWSFs described herein are mixed together before post-processing. For example, different carbon nanoparticles and aggregates containing MWSFs or connected MWSFs with different properties (e.g., different sizes, different compositions, different purities, from different processing runs, etc.) can be mixed together. In some embodiments, the carbon nanoparticles and aggregates containing MWSFs or connected MWSFs described herein could be mixed with graphene to change the ratio of the connected MWSFs to graphene in the mixture. In some embodiments, different carbon nanoparticles and aggregates containing MWSFs or connected MWSFs described herein are mixed together after post-processing. For example, different carbon nanoparticles and aggregates containing MWSFs or connected MWSFs with different properties and/or different post-processing methods (e.g., different sizes, different compositions, different functionality, different surface properties, different surface areas) can be mixed together.

In some embodiments, the carbon nanoparticles and aggregates described herein are produced and collected, and subsequently processed by mechanical grinding, milling, or exfoliating. In some embodiments, the processing (e.g., by mechanical grinding, milling, exfoliating, etc.) reduces the average size of the particles. In some embodiments, the processing (e.g., by mechanical grinding, milling, exfoliating, etc.) increases the average surface area of the particles. In some embodiments, the processing by mechanical grinding, milling or exfoliation shears off some fraction of the carbon layers, producing sheets of graphite mixed with the carbon nanoparticles. In some embodiments, the mechanical grinding or milling is performed using a ball mill, a planetary mill, a rod mill, a shear mixer, high-shear granulator, an autogenous mill, or other type of machine used to break solid materials into smaller pieces by grinding, crushing or cutting. In some embodiments, the mechanical grinding, milling or exfoliating is performed wet or dry. In some embodiments, the mechanical grinding is performed by grinding for some period of time, then idling for some period of time, and repeating the grinding and idling for a number of cycles. In some embodiments, the grinding period is from 1 minute to 20 minutes, or from 1 minute to 10 minutes, or from 3 minutes to 8 minutes, or approximately 3 minutes, or approximately 8 minutes. In some embodiments, the idling period is from 1 minute to 10 minutes, or approximately 5 minutes, or approximately 6 minutes. In some embodiments, the number of grinding and idling cycles is from 1 to 100, or from 5 to 100, or from 10 to 100, or from 5 to 10, or from 5 to 20. In some embodiments, the total amount of time grinding and idling is from 10 minutes to 1200 minutes, or from 10 minutes to 600 minutes, or from 10 minutes to 240 minutes, or from 10 minutes to 120 minutes, or from 100 minutes to 90 minutes, or from 10 minutes to 60 minutes, or approximately 90 minutes, or approximately 120 minutes.

In some embodiments, the grinding steps in the cycle are performed by rotating a mill in one direction for a first cycle (e.g., clockwise), and then rotating a mill in the opposite direction (e.g., counter-clockwise) for the next cycle. In some embodiments, the mechanical grinding or milling is performed using a ball mill, and the grinding steps are performed using a rotation speed from 100 to 1000 rpm, or from 100 to 500 rpm, or approximately 400 rpm. In some embodiments, the mechanical grinding or milling is performed using a ball mill using a milling media with a diameter from 0.1 mm to 20 mm, or from 0.1 mm to 10 mm, or from 1 mm to 10 mm, or approximately 0.1 mm, or approximately 1 mm, or approximately 10 mm. In some embodiments, the mechanical grinding or milling is performed using a ball mill using a milling media composed of metal such as steel, an oxide such as zirconium oxide (zirconia), yttria stabilized zirconium oxide, silica, alumina, magnesium oxide, or other hard materials such as silicon carbide or tungsten carbide.

In some embodiments, the carbon nanoparticles and aggregates described herein are produced and collected, and subsequently processed using elevated temperatures, such as thermal annealing, or sintering. In some embodiments, the processing using elevated temperatures is done in an inert environment such as nitrogen or argon. In some embodiments, the processing using elevated temperatures is done at atmospheric pressure, or under vacuum, or at low pressure. In some embodiments, the processing using elevated temperatures is done at a temperature from 500° C. to 2500° C., or from 500° C. to 1500° C., or from 800° C. to 1500° C., or from 800° C. to 1200° C., or from 800° C. to 1000° C., or from 2000 to 2400° C., or approximately 800° C., or approximately 1000° C., or approximately 1500° C., or approximately 2000° C., or approximately 2400° C.

In some embodiments, the carbon nanoparticles and aggregates described herein are produced and collected, and subsequently additional elements or compounds are added, thereby incorporating the unique properties of the carbon nanoparticles and aggregates into other mixtures of materials. For example, nickel can be added to increase the magnetic permeability of the carbon nanoparticles and aggregates, or the degree of magnetization that the carbon nanoparticles and aggregates obtain in response to an applied magnetic field. Another example is the addition of sulfur to increase the surface area of the carbon nanoparticles and aggregates by forcing the carbon layers to separate. For example, adding sulfur can increase the surface area by 2 or 3 times compared with the material without sulfur. Another method to increase the surface area is through oxidation, however, the resulting compounds (e.g., graphene oxide) are insulators. The methods described herein, e.g., using sulfur, can produce particles with high surface areas that are conductive.

In some embodiments, either before or after post-processing, the carbon nanoparticles and aggregates described herein are added to solids, liquids or slurries of other elements or compounds to form additional mixtures of materials incorporating the unique properties of the carbon nanoparticles and aggregates. In some embodiments, the carbon nanoparticles and aggregates described herein are mixed with other solid particles, polymers or other materials. The resulting powders or composites of the particles in a solid matrix of a different material, can be used in different applications, such as in lubricants or structural composite materials. In some embodiments, the carbon nanoparticles and aggregates described herein are mixed with liquids to produce inks for different applications, such as conductive inks. The resulting inks can also be coated on a substrate or infused in another material for various applications such as capacitor or battery electrodes. In some embodiments, the carbon nanoparticles and aggregates described herein are mixed with solvents and optionally other particles to create slurries, which can then be coated or printed onto other surfaces in various applications, such as printed conductor antennas.

In some embodiments, either before or after post-processing, the carbon nanoparticles and aggregates described herein are used in various applications, including but not limited to lubricant formulations (e.g., lubricants for high-speed or high-stress applications, lubricants for high-temperature environments, lubricants for high-thermal conductivity applications, and anti-stiction lubricants, among others), filtration and separation applications (e.g., chemical filters, water filtration, desalinization, gas separation, oxidation barrier, impermeable membranes, non-reactive filters, and carbon sequestration material, among others), transportation and industrial applications (e.g., rubber additives, tire additives, automobile tire additives, major components in tires, functionalized additives for tires, couplings, mounts, elastomeric o-rings, hoses, sealants, and epoxies, among others), metamaterials formulations (e.g., the particles or aggregates decorated with Ni, Co or Fe nanowires, carbon dielectric layered materials, and interface materials with functionalized surfaces, among other combinations with other materials that result in unexpected properties), electronics ink formulations (e.g., conductive inks, transparent conductive inks, 3D printed circuits and PCBs, resistivity inks, dielectric inks, flexible electronics, piezoelectrics, antennas, rectennas, smart rectennas, electrochromic devices, triboelectric devices, microwave equipment, system inks, and identification systems, among others), other inks (e.g., cosmetics, and 3D printed structural inks, among others), coatings (e.g., anti-corrosion, super hydrophobic, room heating, de-icing, cooling, electro-static discharge (ESD), radiofrequency shielding (EMF shielding) radiofrequency absorbing (EMF absorbing), and fabric and textile coatings, among others), capacitor material formulations (e.g., super capacitor additives, high surface area carbon, high purity carbon, high surface area high purity carbon, and separators, among others), sensors and solid state electronics applications (e.g., chemical, humidity, touch, light, transistors, diodes, and integrated devices, among others), composite materials formulations (e.g., as additives for cement, steel, aluminum, plastics, and carbon fiber, among others), energy applications (e.g., hydrogen storage, anode composites, cathode composites, batteries, fuel cell electrodes, capacitors, and capacitor/battery hybrids, among others), in-vivo bio-medical applications (e.g., tissue engineering, drug delivery, metal delivery, bio-degradable nanowire for neuro regeneration, and better health, among others), and ex-vivo bio-medical applications (e.g., filtration, skin electrodes, and other medical devices).

Examples

Example 1: Experimental Data from Thermal Hot-Wire Processing System

For this example, the carbon nanoparticles and aggregates were generated using a thermal cracking apparatus, described in embodiments above. The thermal cracking apparatus had a main body made from stainless steel with a quartz inner wall material, and a heating element that includes a tantalum/tungsten resistive wire. The reaction zone volume was approximately 2000 cm$^3$. The precursor material was methane, and was flowed from 5 to 10 slm. With those flow rates and the tool geometry, the resonance time of the gas in the reaction chamber was from approximately 0.1 second to 10 seconds, and the carbon particle production rate was from approximately 140 g/hr.

Figure 3A:
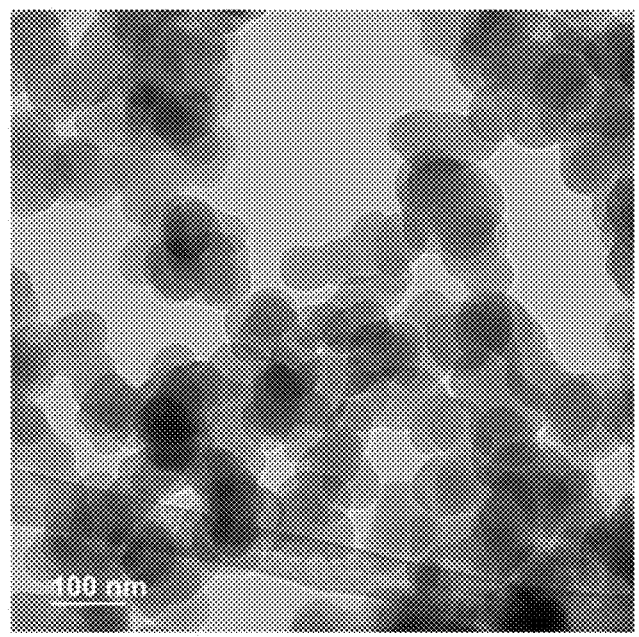
FIGS. 3A-3C show TEM images and Raman spectra from as-synthesized carbon aggregates in a first example, in accordance with some embodiments.
Figure 3B:
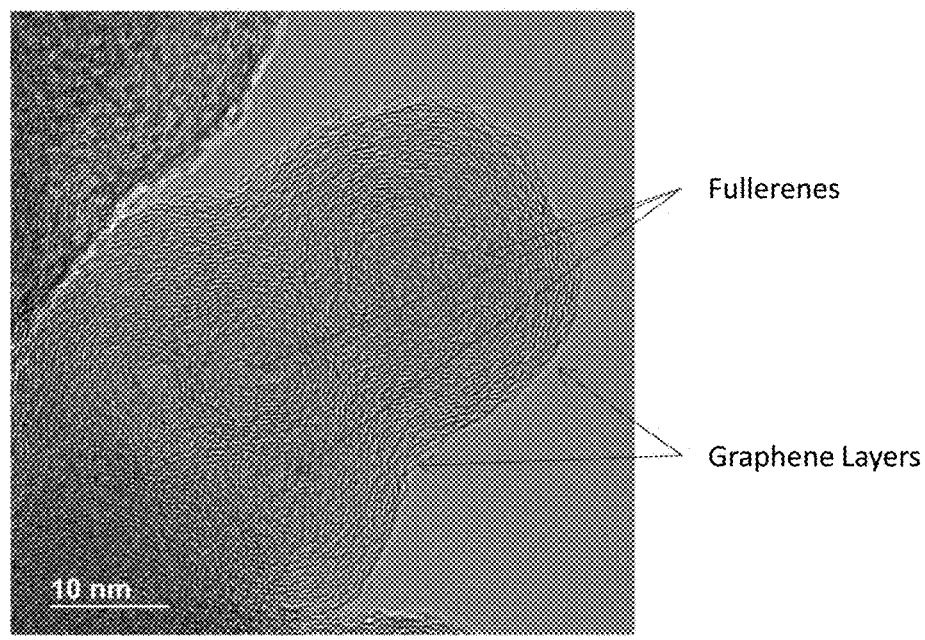
Figure 3C:
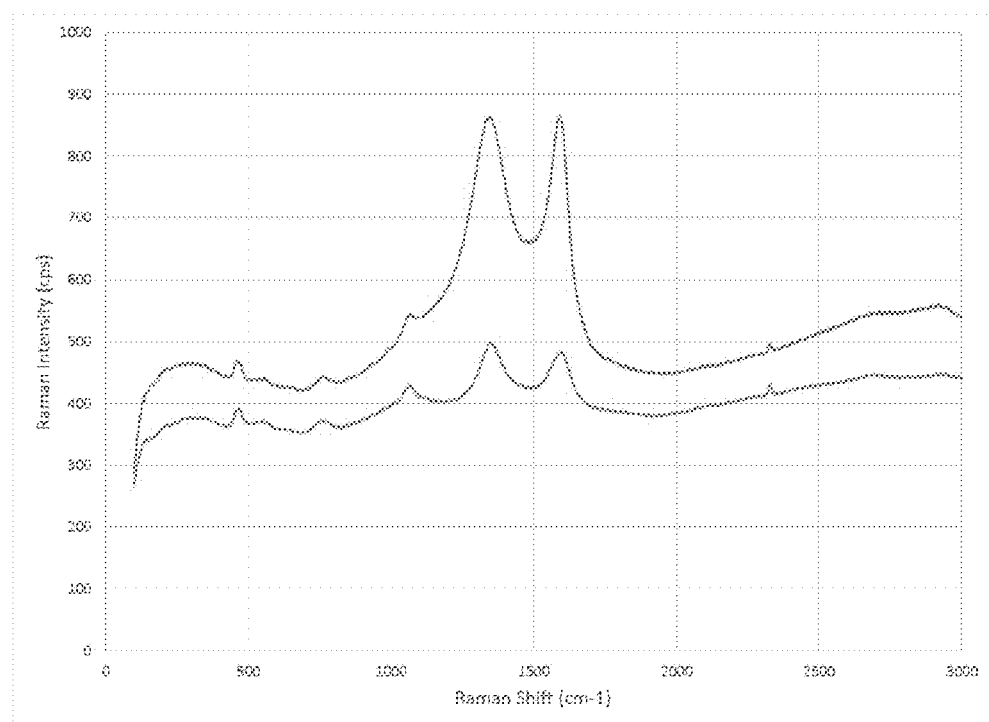

FIGS. 3A and 3B show TEM images of as-synthesized carbon nanoparticles of this example. The carbon nanoparticles contain connected multi-walled spherical fullerenes (MWSFs) with layers of graphene coating the connected MWSFs. The ratio of MWSF to graphene allotropes in this example is approximately 80%, due to the relatively short resonance times. The MWSFs in FIG. 3A are approximately 5-10 nm in diameter, and the diameter can be from 5 to 500 nm using the conditions described above. In some embodiments, the average diameter across the MWSFs is in a range from 5 to 500 nm, or from 5 to 250 nm, or from 5 to 100 nm, or from 5 to 50 nm, or from 10 to 500 nm, or from 10 to 250 nm, or from 10 to 100 nm, or from 10 to 50 nm, or from 40 to 500 nm, or from 40 to 250 nm, or from 40 to 100 nm, or from 50 to 500 nm, or from 50 to 250 nm, or from 50 to 100 nm. No catalyst was used in this process, and therefore, there is no central seed containing contaminants. The aggregate particles produced in this example had particle size of approximately 10 to 100 microns, or approximately 10 to 500 microns. FIG. 3C shows the Raman spectrum of the as-synthesized aggregates in this example taken with 532 nm incident light. The $I_D/I_G$ for the aggregates produced in this example is from approximately 0.99 to 1.03, indicating that the aggregates were composed of carbon allotropes with a high degree of order.

FIGS. 4A and 4B show TEM images of the carbon nanoparticles of this example after size-reduction by grinding in a ball mill. The ball milling was performed in cycles with a 3 minute counter-clockwise grinding step, followed by a 6 minute idle step, followed by a 3 minute clockwise grinding step, followed by a 6 minute idle step. The grinding steps were performed using a rotation speed of 400 rpm. The milling media was zirconia, and ranged in size from 0.1 mm to 10 mm. The total size reduction processing time was from 60 to 120 minutes. After size-reduction, the aggregate particles produced in this example had particle size of approximately 1 to 5 microns. The carbon nanoparticles after size-reduction are connected MWSFs with layers of graphene coating the connected MWSFs. FIG. 4C shows a Raman spectrum from the aggregates of this example after size-reduction taken with a 532 nm incident light. The $I_D/I_G$ for the aggregate particles in this example after size-reduction is approximately 1.04. Additionally, the particles after size-reduction had a Brunauer, Emmett and Teller (BET) specific surface area of approximately 40 to 50 m$^2$/g.

The purity of the aggregates produced in this sample were measured using mass spectrometry and x-ray fluorescence spectroscopy (XRF). The ratio of carbon to other elements, except for H, measured in 16 different batches was from 99.86% to 99.98%, with an average of 99.94%.

Example 2: Experimental Data from Thermal Hot-Wire Processing System

In this example, carbon nanoparticles were generated using a thermal hot-wire processing system described in Example 1. The precursor material was methane, and was flowed from 1 to 5 slm. With those flow rates and the tool geometry, the resonance time of the gas in the reaction chamber was from approximately 20 second to 30 seconds, and the carbon particle production rate was from approximately 20 g/hr.

Figure 5A:
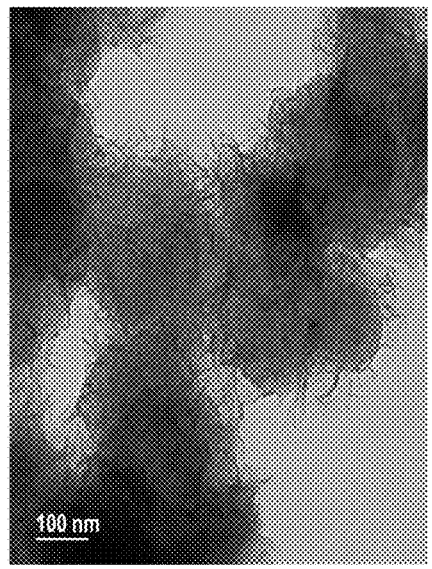
FIGS. 5A-5D show TEM images and Raman spectra from as-synthesized carbon aggregates in a second example, in accordance with some embodiments.
Figure 5B:
Figure 5C:
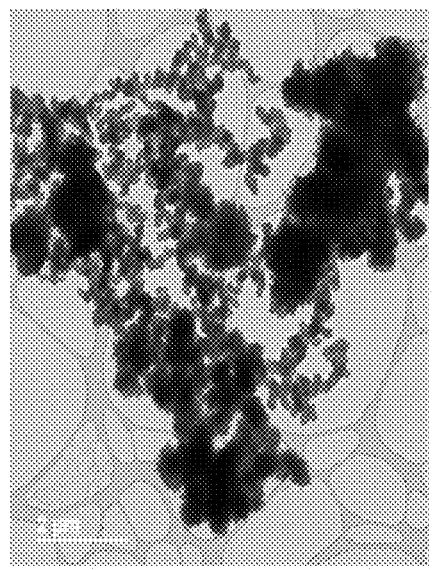
Figure 5D:
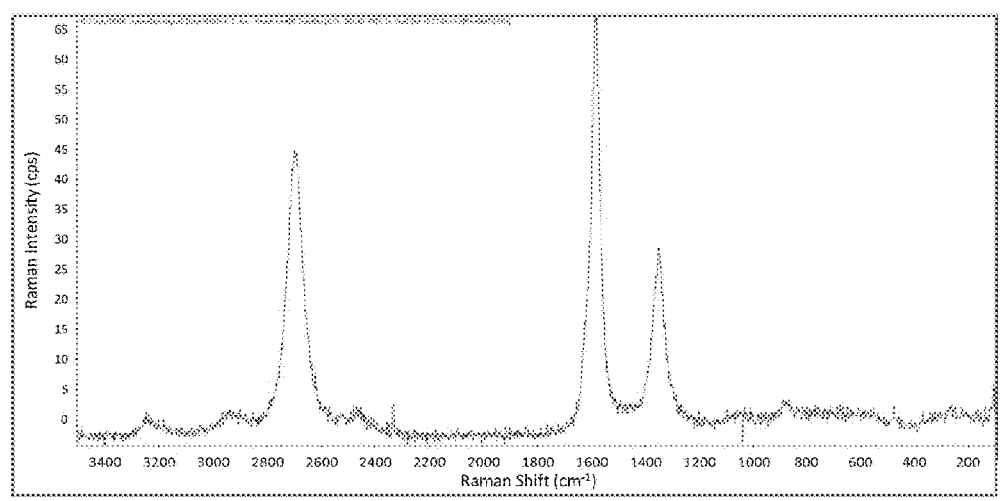

FIGS. 5A, 5B and 5C show TEM images of as-synthesized carbon nanoparticles of this example. The carbon nanoparticles contain connected multi-walled spherical fullerenes (MWSFs) with layers of graphene coating the connected MWSFs. The ratio of multi-walled fullerene to graphene allotropes in this example is approximately 30%, due to the relatively long resonance times allowing thicker, or more, layers of graphene to coat the MWSFs. No catalyst was used in this process, and therefore, there is no central seed containing contaminants. The as-synthesized aggregate particles produced in this example had particle size of approximately 10 to 500 microns. FIG. 5D shows a Raman spectrum from the aggregates of this example. The Raman signature of the as-synthesized particles in this example is indicative of the thicker graphene layers which coat the MWSFs in the as-synthesized material. Additionally, the as-synthesized particles had a Brunauer, Emmett and Teller (BET) specific surface area of approximately 90 to 100 m$^2$/g.

Figure 6A:
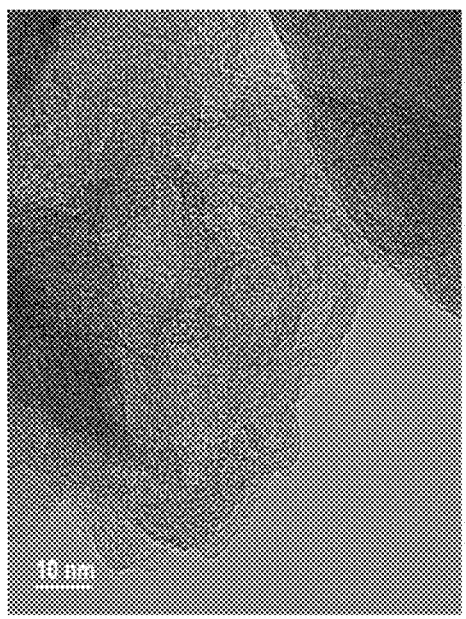
FIGS. 6A-6C show TEM images and Raman spectra from size-reduced carbon aggregates in a second example, in accordance with some embodiments.
Figure 6B:
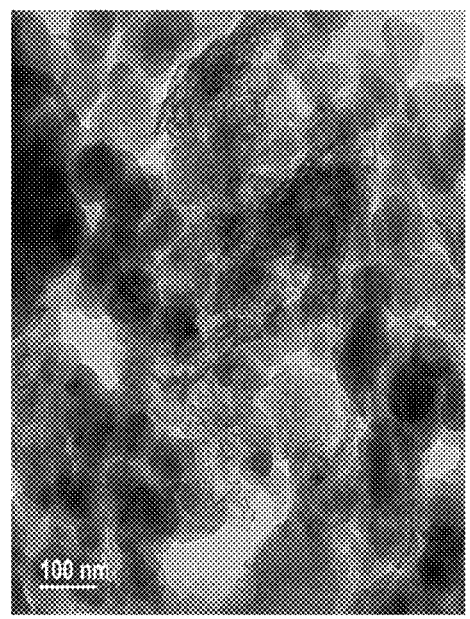
Figure 6C:
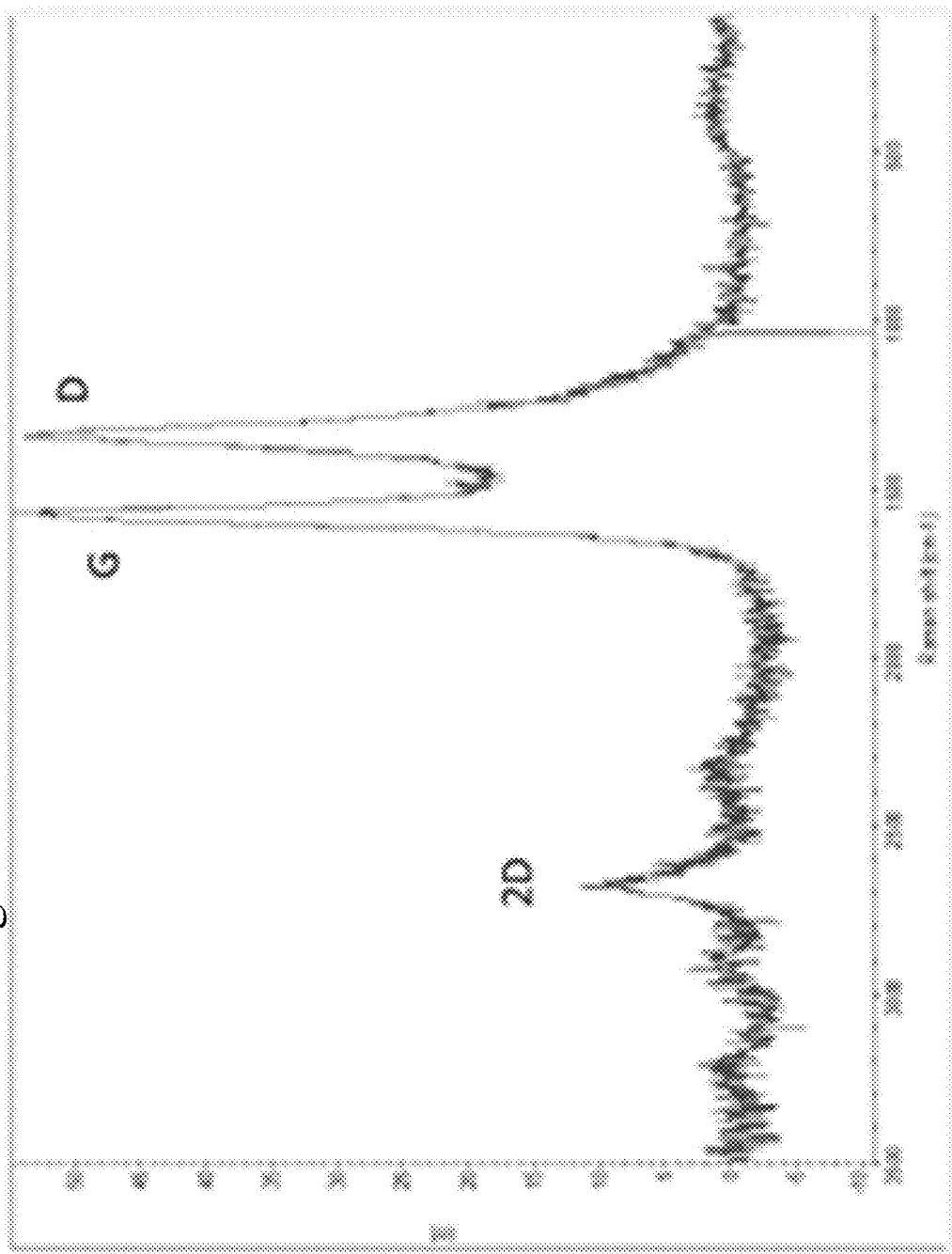

FIGS. 6A and 6B show TEM images of the carbon nanoparticles of this example after size-reduction by grinding in a ball mill. The size-reduction process conditions were the same as those described in Example 1. After size-reduction, the aggregate particles produced in this example had particle size of approximately 1 to 5 microns. The TEM images show that the connected MWSFs that were buried in the graphene coating can be observed after size-reduction. FIG. 6C shows a Raman spectrum from the aggregates of this example after size-reduction taken with 532 nm incident light. The $I_D/I_G$ for the aggregate particles in this example after size-reduction is approximately 1, indicating that the connected MWSFs that were buried in the graphene coating as-synthesized had become detectable in Raman after size-reduction and were well-ordered. The particles after size-reduction had a Brunauer, Emmett and Teller (BET) specific surface area of approximately 90 to 100 m$^2$/g.

Reference has been made in detail to embodiments of the disclosed invention, one or more examples of which have been illustrated in the accompanying drawings. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention. Furthermore, those of ordinary skill in the art will appreciate that the foregoing description is by way of example only, and is not intended to limit the invention.

What is claimed is:

1. A carbon nanoparticle comprising:
   at least two connected multi-walled spherical fullerenes; and
   layers of graphene coating the connected multi-walled spherical fullerenes;
   wherein:
   a Raman spectrum of the carbon nanoparticle using 532 nm incident light has a first Raman peak at approximately 1350 cm$^{-1}$ and a second Raman peak at approximately 1580 cm$^{-1}$, and a ratio of an intensity of the first Raman peak to an intensity of the second Raman peak is from 0.9 to 1.1.

2. The carbon nanoparticle of claim 1, wherein:
   the multi-walled spherical fullerenes do not comprise a seed particle or a void at the center of the multi-walled spherical fullerenes.

3. The carbon nanoparticle of claim 1, wherein:
   the multi-walled spherical fullerenes have an average diameter from 50 nm to 500 nm.

4. A carbon aggregate comprising a plurality of the carbon nanoparticles of claim 1, wherein:
   a diameter across the carbon aggregate is from 10 microns to 500 microns.

5. The carbon aggregate of claim 4, wherein:
   the ratio of graphene to multi-walled spherical fullerenes is from 10% to 80%.

6. The carbon aggregate of claim 4, wherein:
   a ratio of carbon to other elements, except H, in the carbon aggregate is greater than 99.9%.

7. The carbon aggregate of claim 4, wherein:
   a Brunauer, Emmett and Teller (BET) specific surface area of the carbon aggregate is from 10 m$^2$/g to 200 m$^2$/g.

8. The carbon aggregate of claim 4, wherein:
   a plurality of the carbon aggregates are compressed into a pellet, and the pellet has an electrical conductivity from 500 S/m to 20000 S/m.

9. A carbon nanoparticle comprising:
   at least two connected multi-walled spherical fullerenes; and
   layers of graphene coating the connected multi-walled spherical fullerenes;
   wherein a ratio of graphene to multi-walled spherical fullerenes is from 10% to 80%.

10. A mixture comprising a liquid and a plurality of the carbon nanoparticles of claim 9.

11. A conductive ink comprising a plurality of the carbon nanoparticles of claim 9.

12. A carbon aggregate comprising a plurality of the carbon nanoparticles of claim 9, wherein:
    a diameter across the carbon aggregate is from 10 microns to 500 microns.

13. The carbon aggregate of claim 12, wherein:
    a ratio of carbon to other elements, except H, in the carbon aggregate is greater than 99.9%.

14. The carbon aggregate of claim 12, wherein:
    a Brunauer, Emmett and Teller (BET) specific surface area of the carbon aggregate is from 10 m$^2$/g to 200 m$^2$/g.

15. The carbon aggregate of claim 12, wherein:
    the aggregates are compressed into a pellet, and the pellet has an electrical conductivity from 500 S/m to 20000 S/m.

16. A method comprising:
    flowing a hydrocarbon feedstock process gas into a reaction zone;
    thermally cracking molecules of the feedstock process gas in the reaction zone;
    reacting the thermally cracked molecules to form carbon aggregates, each comprising at least two connected multi-walled spherical fullerenes coated in layers of graphene; and
    collecting the carbon aggregates;
    wherein:
    a Raman spectrum of the carbon aggregates using 532 nm incident light has a first Raman peak at about 1350 cm$^{-1}$ and a second Raman peak at about 1580 cm$^{-1}$, and
    a ratio of an intensity of the first Raman peak to an intensity of the second Raman peak is from 0.9 to 1.1.

17. The method of claim 16, further comprising:
    size-reducing the carbon aggregates by mechanical processing.

18. The method of claim 16, wherein:
    the multi-walled spherical fullerenes do not comprise a seed particle or a void at the center of the multi-walled spherical fullerenes.

19. The method of claim 16, wherein:
    an average diameter across the carbon aggregates is from 10 microns to 500 microns.

20. The method of claim 16, wherein:
    the multi-walled spherical fullerenes have an average diameter from 50 nm to 500 nm.

21. The method of claim 16, wherein:
    a ratio of graphene to multi-walled spherical fullerenes is from 10% to 80%.

22. The method of claim 16, wherein:
    a ratio of carbon to other elements, except H, in the carbon aggregates is greater than 99.9%.

23. The method of claim 16, wherein:
    a Brunauer, Emmett and Teller (BET) specific surface area of the carbon aggregates is from 10 m$^2$/g to 200 m$^2$/g.

24. The method of claim 16, further comprising:
    compressing the carbon aggregates into a pellet, wherein the pellet has an electrical conductivity from 500 S/m to 20000 S/m.

25. The method of claim 16, further comprising:
    forming the carbon aggregates with a gas resonance time of 0.1 seconds to 30 seconds.

26. The method of claim 16, further comprising:
forming the carbon aggregates with a gas flow rate of 1 slm to 10 slm and a production rate from 10 g/hr to 200 g/hr.

27. The method of claim 16, further comprising, post-processing the carbon aggregates using a method selected from group consisting of milling, grinding, exfoliating, annealing, sintering, steaming, filtering, lypolizing, doping, and adding elements.

* * * * *